United States Patent [19]

Nordquist et al.

[11] Patent Number: 4,959,489
[45] Date of Patent: Sep. 25, 1990

[54] PROCESS FOR MAKING AN ACRYLAMIDE CONTAINING A DIALKYL ACETAL GROUP

[75] Inventors: Andrew F. Nordquist; Robert K. Pinschmidt, Jr., both of Whitehall, Pa.

[73] Assignee: Air Products and Chemicals, Inc., Allentown, Pa.

[21] Appl. No.: 416,289

[22] Filed: Oct. 2, 1989

[51] Int. Cl.$^5$ .................. C07C 229/30; C07C 231/02
[52] U.S. Cl. .................................... 560/170; 564/135; 564/136
[58] Field of Search ................. 564/135, 136; 560/170

[56] References Cited

U.S. PATENT DOCUMENTS

| | | | |
|---|---|---|---|
| 2,451,436 | 10/1948 | Erickson | 260/561 |
| 2,529,838 | 11/1950 | Erickson | 260/561 |
| 2,587,209 | 2/1952 | Phillips et al. | 260/561 |
| 2,719,178 | 9/1955 | Coover, Jr. et al. | 260/562 |
| 3,878,247 | 4/1975 | Moss et al. | 260/561 |
| 3,914,303 | 10/1975 | Daniher et al. | 260/561 |
| 4,206,143 | 6/1980 | Wenzel et al. | 564/135 |
| 4,549,017 | 10/1985 | Mc Entire et al. | 544/168 |
| 4,644,083 | 2/1987 | Dahmen et al. | 564/205 |
| 4,663,410 | 5/1987 | Pinschmidt et al. | 526/263 |
| 4,691,026 | 9/1987 | Pinschmidt et al. | 548/531 |
| 4,831,153 | 5/1989 | Phung | 548/231 |

FOREIGN PATENT DOCUMENTS 728955  4/1965  United Kingdom .
2100732  8/1985  United Kingdom .

OTHER PUBLICATIONS

"Kinetics of Reversible Endothermic Elimination Reactions: Beta-Amino Carboxylic Esters and Amides," M. R. Johnson, J. Org. Chem., p. 833-837, (1986).

Primary Examiner—Glennon H. Hollrah
Assistant Examiner—Susan P. Treanor
Attorney, Agent, or Firm—Mark L. Rodgers; William F. Marsh; James C. Simmons

[57] ABSTRACT

A process is provided for making an N-substituted acrylamide dialkyl acetal, such as acrylamidobutyraldehyde dimethylacetal (ABDA), by blocking the double bond in an acrylic acid ester with a nucleophile, such as methanol, removing excess nucleophile from the blocked ester, aminating the blocked ester with an amino dialkyl acetal in the presence of an aminolysis catalyst but in the absence of any protic solvent, and deblocking the double bond in the product by pyrolysis.

11 Claims, No Drawings

PROCESS FOR MAKING AN ACRYLAMIDE CONTAINING A DIALKYL ACETAL GROUP

TECHNICAL FIELD

This invention relates to a method of making an N-substituted acrylamide containing acid sensitive groups. In another aspect it relates to a method of preparing N-substituted acrylamides from amines which contain a dialkyl acetal group.

BACKGROUND OF THE INVENTION

Polymerizable N-substituted amides, and more specifically N-olefinically unsaturated amidodialkyl acetals, are useful monomers for free radical polymerization, especially with comonomers such as ethylene, vinyl acetate, vinyl chloride, and the like. Such acrylamides which contain the dialkyl acetal group are able to introduce into polymers the capability of internal crosslinking without the side production of formaldehyde. These polymers have found utility in a number of areas including binders, adhesives and coatings. In this regard, the acetal functionality is particularly desirable.

U.S. Pat. Nos. 4,663,410 and 4,691,026, Pinschmidt et al., (1987) disclose the preparation of acrylamidobutyraldehyde dimethylacetal (ABDA) by the reaction of amines and acid chlorides in the presence of a base to remove the hydrogen chloride which is formed in the reaction. The utility of the acrylamides containing dimethylacetal groups is also demonstrated. These patents also suggest other methods for preparing the valuable monomer, such as by the addition of aminoacetal compounds to maleic anhydride in an inert solvent or by reacting an olefinically unsaturated carboxylic acid with an aminoacetal or ketal using dehydrating agents, such as $SOCl_2$ or carbodiimides. One of the alternate routes suggested is the reaction of an alkylamine with alkyl acrylates to give acrylamides. This reaction, however, involves Michael addition of the amine to the double bond, which is reversible at higher temperatures allowing net formation of N-alkylacrylamides. It is further suggested that the Michael reaction can be suppressed by preforming reversible alcohol or alkylamine acrylate adducts. Such a procedure would be very attractive because it requires much less expensive feedstocks than the acryloyl chlorides of the principle method disclosed by these patents. The problem, however, has been consistently inadequate yields because of the inability to suppress or circumvent the Michael reaction.

In general, the reaction of alkylamines with acrylate esters has been known for decades. For example, U.S. Pat. No. 2,451,436 to Erickson (1948) discloses the reaction of n-butylamine with ethyl acrylate and the conversion of the N-alkyl-$\beta$-alkylaminopropionamide by heating in the presence of an acid, for example sulfuric acid to split off the alkylamine salt which is formed as a part of the Michael reaction. This leaves N-alkyl-$\alpha,\beta$-unsaturated amide, such as N-n-butylacrylamide. Even though the best yields disclosed are only about 75%, the conditions and particularly the acidic conditions required would not be suitable for the reaction of amines containing acetal groups which are not stable under such acidic conditions.

U.S. Pat. No. 2,529,838 Erickson (1950), discloses making N,N-dialkylacrylamides by heating an acrylic ester with an dialkylamine, where the alkyl groups must contain five or more carbon atoms. The example, however, shows only about 10% yield.

U.S. Pat. No. 2,587,209 to Phillips et al., (1952), discloses that $\beta$-(lower alkoxy)propionamides can be dealcoholated catalytically in the vapor phase to acrylamides. U.K Pat. No. 728,955 (1955) also discloses a vapor phase thermal disassociation of derivatives of propionamides, but neither of these references which describe vapor phase deblocking of the double bond of the acrylamide suggest application of the process to compounds which contain acetal groups.

U.S. Pat. No. 2,719,178 to Coover et al., (1955), discloses that N-alkyl-$\beta$-N-alkylaminopropionamides can be converted to the corresponding unsaturated $\alpha,\beta$-unsaturated amides by pyrolysis of the vaporized feed at 300° to 550° C., using a suitable catalyst such as alumina silica, with or without a diluent. These conditions are far too extreme for acetals and could not be used with compounds which contain the dialkyl acetal groups such as those which have been described to be highly useful comonomers in the patents to Pinschmidt et al., cited above.

U.S. Pat. No. 3,878,247 to Moss et al, (1975) describes a noncatalytic process for preparing N-(tertiaryaminoalkyl)acrylamides. The process starts by reacting a tertiaryaminoalkyl amine with an acrylic acid or ester at about 100° to 200° C. to form a beta-aminopropionamide, which is then converted by heating at 180° to 300° C. to the N-(tertiaryaminoalkyl)acrylamide. Example II of this reference describes the cracking of the 3-dimethylaminopropylamine Michael adduct of N-(3-dimethylaminopropyl)acrylamide at 205° to 275° C. followed by distillation of the product mix of amine and amide to obtain the amide in 72% yield. To attempt such a reaction with a primary amine having dialkylacetal groups under such drastic cracking conditions, would give severe product decomposition. Also rapid back-reaction of the product acrylamide with coproduct primary amine makes the acrylamide isolation impossible with acceptable yields.

One possible route following the suggestion in the Pinschmidt et al., patents is to use a blocking technique to suppress the Michael reaction. This approach has been used as described in U.S. Pat. No. 3,914,303 to Daniher et al., (1975) which describes preparing N,N-dialkylamide of an $\alpha,\beta$-olefinically unsaturated monocarboxylic acid. The procedure requires the use of a polyol solvent-catalyst for the amidation reaction between the $\beta$-ether-substituted monocarboxylic acid ester and the dialkyl amine. Glycerin is given as a preferred solvent-catalyst. It is stated that non-catalytic amidation at 100° to 125° C. resulted in byproduct formation of appreciable amounts of $\beta$-methoxypropionic acid. Use of the polyol is said to minimize side reactions and increase yield. Pyrolysis, however, is used to convert the $\beta$-ether-substituted amide to the unsaturated amide forming, for example, N,N-dimethyl $\beta$-methoxypropionamide which is converted to N,N-dimethylacrylamide using an acid cracking catalyst. This technique would destroy an amide which contained dialkyl acetal groups.

More recently, attempts have been made to go directly to the N-substituted amide of acrylic or methacrylic acid by reacting an alkyl ester of acrylic or methacrylic acid with an amine. Such a procedure is described in U.K. Pat. No. 2,100,732 (1985) which further describes the reaction as carried out over a catalyst of a compound of metals of Group IV, zinc or tantalum.

While the conditions are said to be particularly suitable when using primary or secondary amines or compounds such as alkylenediamines, no mention is made of amines which contain acetal groups. Although yields as high as 80% were reported, the Michael adduct was still formed.

U.S. Pat. No. 4,549,017 to MacIntyre et al.. (1985) discloses a process for making N-substituted acrylamides by reacting an acrylate ester with an amine over an alkyl metal oxide or alkoxide. The advance described is in the use of a drying agent to completely remove water from the feedstocks. It is stated that by avoiding water, the Michael reaction can be reduced.

U.S. Pat. No. 4,644,083 to Dahmen et al., (1987) discloses that polyvalent alcohols, such as ethylene glycol or glycerin, can be added to unsubstituted $\alpha,\beta$-unsaturated carboxylic acid amides, such as acrylamide, using base catalysis and the product is transamidated with a primary or secondary amine in the presence of catalytic amounts of carboxylic acid. The N-substituted-$\beta$-saturated propionamides are then decomposed pyrolytically to N-substituted $\alpha,\beta$-unsaturated carboxylic acid amides. But there is no disclosure of using amines containing acetal groups and, in fact, the acidic transamidation described would decompose such acetal groups.

As can be seen from the above discussed references, a temporary protection of a double bond in an activated olefin by Michael addition of an alcohol is a known method of preventing undesired reactions at the double bond while the resulting adduct is subjected to other reaction conditions. This type of protection has been used to block the double bond in acrylic esters during aminolysis of the ester, to form the 3-alkoxy propionamide. Since Michael addition of either alcohols or amines to olefins is reversible under addition conditions, controlled conditions to avoid premature loss of protection or deblocking is critical. When the olefin is blocked with an alcohol, the addition reaction can be driven to greater than 99% completion by the use of excess alcohol. An excess of alcohol, therefore, might be expected to prevent loss of the alcohol blocking group. Johnson, J. Org. Chem., 51, 883–837 (1986) discloses that amines react with $\alpha,\beta$-unsaturated ketones, esters, amides and sulfones in the synthesis of substituted acrylamides and that the reaction is reversible. Kinetics are reported on the reaction in methanol.

BRIEF DESCRIPTION OF THE INVENTION

We have discovered a process for making acrylamide compounds containing dialkyl acetal groups without destroying these acid sensitive groups and without using expensive starting materials, such as the acid chlorides which are described in the patents to Pinschmidt et al., cited above. According to our invention the acrylamide dialkyl acetal is formed by (a) reacting an acrylic acid ester with a nucleophile to form a $\beta$-substituted propionate, (b) separating any excess nucleophile from said $\beta$-substituted propionate, (c) reacting said $\beta$-substituted propionate with an aminodialkyl acetal in the presence of an aminolysis catalyst and in the absence of a protic solvent in order to form a $\beta$-substituted propionamide dialkyl acetal, and then (d) pyrolyzing the $\beta$-substituted propionamide dialkyl acetal to form an acrylamide dialkyl acetal. The pyrolysis can be carried out under relatively mild conditions without the use of acidic catalysts and by avoiding the presence of a protic solvent during the aminolysis, the protection of the blocking reaction with the nucleophile is preserved and Michael addition to form a byproduct with the amine is avoided. Yields of the product are thereby improved and the desired dialkyl acetal group is likewise preserved in the final product.

DETAILED DESCRIPTION OF THE INVENTION

According to our invention the need for an economical synthetic route to N-substituted acrylamides containing the acid sensitive groups, dialkyl acetals, is provided in an efficient manner. For example, acrylamidobutyraldehyde dimethylacetal (ABDA) is a monomer very useful for crosslinking when incorporated into copolymers such as with vinyl acetate or vinyl acetate and ethylene. In the process of our invention, an acrylic acid ester is first reacted with a nucleophile yielding, by Michael addition, a $\beta$-substituted propionate. The $\beta$-substituted propionate is then aminolyzed in the presence of a catalyst in a solvent-free system, producing a $\beta$-substituted propionamide which is then pyrolyzed to yield the acrylamide containing the dialkyl acetal group.

In the first step of the blocking reaction with the acrylic acid ester, the ester preferably has the formula

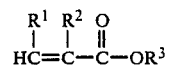

wherein $R^1$ is hydrogen, alkyl, cycloalkyl or aryl having up to 6 carbons or $-COOR^4$; $R^2$ is hydrogen, alkyl, cycloalkyl or aryl having up to 6 carbons, but at least one of $R^1$ and $R^2$ is hydrogen; and $R^3$ and $R^4$ are each alkyl of 1 to 4 carbons or phenyl.

It should be understood that any of several esters containing olefinic unsaturation which can be activated for nucleophilic additions, can be used as a feedstock. For example, such esters include the $\alpha$-substituted acrylates (such as methacrylates, $\alpha$-aryl acrylates or $\alpha$-alicylic acrylates), and $\beta$-substituted acrylates, such as crotonates, maleates, fumarates or cinnamates. Because of the lower reactivity of the olefinic group in substituted acrylates the tendency to Michael addition with $\alpha$ or $\beta$ substituted acrylates is not as great as with unsubstituted acrylates.

The alcohol portion of the acrylic ester can be derived from any of the low boiling alcohols, preferably $C_1-C_4$ saturated alcohols. The methyl esters are most preferred because of the volatility of the byproduct methanol which allows easy removal from the reaction system. Esters of higher boiling alcohols such as butanols, and phenols are operable, but are less preferred, and hindered alcohols such as t-butanol are still operable but less desirable because of difficulty in aminolysis.

Any nucleophile which can be added by Michael addition to an activated olefin and is stable under the disclosed aminolysis conditions and can be removed pyrolytically under mild, non-acidic conditions to regenerate the double bond, can be used for the double bond blocking or protection and is acceptable. Such nucleophiles include alcohols, phenols, primary or secondary amines, sulfides, phosphines, cyanides, malonates, acetates, halides, silanols, nitroalkanes, amine oxides, and the like. Methanol, however, is by far the preferred nucleophile because of the ease with which it can be separated from the product. Any well known catalyst for this addition can be used, such as an alkali metal alkoxide, but sodium methoxide is the preferred catalyst, particularly for use with methanol.

Following the reaction of the acrylic acid ester with an nucleophile under catalytic conditions any unreacted nucleophile is separated from the blocked ester. This step can be easily performed by evaporation as demonstrated by the examples which employ rotary evaporation under reduced pressures.

In the next step of the process the blocked ester from which any unreacted nucleophile has been removed is aminated with an aminodialkyl acetal in the presence of an aminolysis catalyst and in the absence of any other protic solvent. Preferably the aminodialkyl acetal has the structural formula:

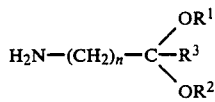

wherein $R^1$ and $R^2$ are each alkyl of 1 to 4 carbons, $R^3$ is hydrogen or alkyl of 1 to 4 carbons, and n is an integer of 1 to 10.

The most preferred amine is aminobutyraldehyde dimethyl acetal (AmBDA), but similar compounds falling within the structural formula given can be used.

A preferred aminolysis catalyst for use in this process is an oxide, alkoxide or alkyloxide of titanium, zirconium, zinc, aluminum, tin lead, antimony, bismuth, lithium, sodium, potassium, magnesium, calcium, strontium or barium. Any such aminolysis catalyst which does not promote Michael addition can suffice. Examples include methoxides, ethoxides, propoxides, isopropoxides, butoxides, and the like, of the metals named and metal oxides, such as dibutyl tin oxide. These catalysts are used in the usual catalytic amounts, normally about 0.001 to 0.2 moles per mole of amine and preferably about 0.01 to 0.08 moles of catalyst per mole of amine. Lesser amounts of catalyst can be used, e.g. down to as low as 0.0001 mole per mole, depending upon the catalyst activity. The aminolysis is carried out by warming the reaction mixture to a temperature in the range of about 70° to 120° C. Following the reaction, the by-product methanol is removed by distillation. The distillation temperature can be from 20° to 200° C., although the temperature should not exceed that at which the dialkyl acetal groups on the amide are stable. The preferred temperature range for this byproduct methanol removal is about 70° to 130° C.

Although protic solvents are to be avoided in this reaction, non-protic solvents can be employed in the aminolysis mixture. For example, high boiling ethers such as glymes, aromatic hydrocarbons and saturated or unsaturated hydrocarbons can be used, but use of any solvent is not necessary.

Following the aminolysis reaction and recovery of the aminated product, the product is pyrolyzed under non-acidic conditions in order to restore the double bond and form the N-substituted acrylamide. One suitable method for carrying out the pyrolysis involves the use of calcium carbonate. Although such material is not essential, there is an advantage in using such a weakly basic, high surface area material for the pyrolysis. The acetal substituted amides are unstable under acidic conditions, but have been shown to be quite stable over this support.

Our invention can be better understood by reference to the following examples which are presented for illustrative purposes and to demonstrate the advantages of our invention and should not be construed to limit the invention unduly.

EXAMPLE 1

Methyl 3-methyoxypropionate

Dry methyl acrylate (95.5 g, 1.11 moles) and 200 mL of dry methanol were combined with 0.53 g (9.82 mmoles) of sodium methoxide and stirred at 20° C. for 16 hours. After 16 hours, when conversion to methyl 3-methoxypropionate (MMP) was 97% complete by capillary gas chromatography, 0.18 g (10 mmoles) of water was added. Excess methanol, along with some MMP was removed by rotary evaporation at 40° C. and 20 torr. MMP was short-path distilled from the resulting concentrate at 40° C. and 40 mtorr, producing 171 g of colorless liquid (65% recovered yield). Analysis of the product by NMR showed: $^1H$ nmr (COCl$_3$); $\delta$3.30 (s, ether OCH$_3$), $\delta$2.52 (t, OCH$_2$), $\delta$3.60 (t, CH$_2$), and $\delta$3.63 ppm (s, ester OCH$_3$) in the expected 3/2/2/3 ratio.

EXAMPLE 2

3-Methoxypropionamidobutyraldehyde Dimethyl Acetal

Aminobutyraldehyde dimethyl acetal, AmBDA, (133 g=1.0 mole) and 118 g (1 mole) of MMP were heated at 100° C. with 6.48 g (0.023 moles) of titanium isopropoxide in a flask equipped with a water cooled condenser. After hours, the product contained 67.5 wt % methoxypropionamidobutyraldehyde dimethyl acetal (MPBDA) and 7.3 wt % AmBDA (79.4% yield, 85.9% AmBDA conversion). By-product methanol, unreacted MMP, and most unreacted AmBDA were removed from the reaction mix by Kugelrohr distillation at 110° C.-120° C., producing a 96 wt % MPBDA, 1 wt % AmBDA solution.

EXAMPLES 3-6

Pyrolysis of MPBDA to ABDA

MPBDA prepared in Example 2 was vacuum pyrolyzed as follows: A mixture of 47.9 g of MPBDA, 0.50 g of AmBDA, 0.1089 g of phenothiazine, and 5.00 g of tetraglyme (internal standard) was fed through a flow restricting orifice into the evacuated zone of a heated 9 mm I.D. quartz column packed with 15.12 g (17 cm bed length) of 12/16 tyler mesh CaCO$_3$. The least volatile liquid products were condensed in an air cooled receiver at the bottom of the column and byproduct methanol was trapped in a −190° C. trap evacuated between 50 and 250 mtorr. Results are shown in Table I.

TABLE I

| Example | Column Temp. (°C.) | g. MPBDA g Cat. h | Column Length (cm) | MPBDA Conv. (%) | ABDA Yield (%) | ABDA Sel. (%) | Recovery (%) |
|---|---|---|---|---|---|---|---|
| 3* | 150 | 1.50 | 9.5 | 36.9 | 21.4 | 58.0 | 84.5 |
| 4 | 200 | 0.78 | 9.5 | 83.1 | 83.1 | 100.0 | 100.0 |
| 5 | 250 | 0.85 | 9.5 | 70.6 | 63.9 | 90.5 | 97.0 |

TABLE I-continued

| Example | Column Temp. (°C.) | g. MPBDA g Cat. h | Column Length (cm) | MPBDA Conv. (%) | ABDA Yield (%) | ABDA Sel. (%) | Recovery (%) |
|---|---|---|---|---|---|---|---|
| 6 | 250 | 0.62 | 17.0 | 99.1 | 92.3 | 93.1 | 93.1 |

*column not equilibrated

EXAMPLE 7

A stirred, nitrogen blanketed flask equipped with a distillation head was charged with 39.43 g (0.334 moles) of MMP prepared in Example 2, 13.33 g of AmBDA (0.10 mole) and 2.65 g of N-methylpyrrolidinone as internal standard. Titanium isopropoxide (1.9283 g, 6.79 mmoles) was added and the reaction mixture was heated at 100° C. After 17 hours the reaction mix was analyzed by capillary gas chromatography; 98.3% of the AmBDA had been converted with 100% selectivity to MPBDA.

Examples 8 and 9 illustrate that protic solvents cause loss of the blocking group from the double bond and promote Michael addition of the amine to the olefin, and thus decrease aminolysis selectivity.

EXAMPLE 8

Dry methyl acrylate (47.8 g, 0.555 moles) and 100 mL of dry methanol were combined with 0.0307 g (0.67 mmoles) of sodium methoxide and stirred at 20° C. After 40 hours, conversion to methyl 3-methoxypropionate (MMP) was 99% complete by capillary gas chromatography. A stirred, nitrogen blanketed flask equipped with a distillation head was charged with 106.5 g of the above MMP/methanol solution, 2.1449 g (7.17 mmoles) of titanium isopropoxide was added, and the reaction vessel heated to 70° C. Over the next 100 minutes while maintaining the temperature at 70° C., a solution containing 13.82 g of AmBDA and 3.06 g of N-methylpyrrolidinone (internal standard) was added and distillate was removed from the reaction. Over the next 2 hours the temperature was increased to 95° C. after which MPBDA yield was 10.7%. After an additional 17 hours the MPBDA yield was 45.1% and Michael adduct yield was 41.4%.

EXAMPLE 9

Dry methyl acrylate (47.8 g, 0.555 moles) and 100 mL methanol were combined with 0.3138 g (5.81 mmoles) of sodium methoxide and stirred at 20° C. After 17 hours, conversion to methyl 3-methoxypropionate (MMP) was 99% complete by capillary gas chromatography. AmBDA (77.21 g, 0.581 moles) was added to the above reaction mix at 30° C. over 45 minutes and the reaction mixture was heated at 82° C. for 4 hours, after which AmBDA conversion was 70.5% with 53.8% selectivity to MPBDA and 46.2% selectivity to Michael adduct. After several days at room temperature, 75.6% of the AmBDA was converted with 60.7% selectivity to MPBDA and 21.5% selectivity to heavier Michael addition products detectable by gas chromatography.

While we are not to be limited by theory, it is believed that the nucleophile, and specifically methanol, is catalytic for both the addition of the nucleophiles to activated olefins and for the elimination of the nucleophiles from the olefin. This conclusion would be supported by the conclusion of Johnson, cited above, to the effect that protic solvents participate in the Michael addition mechanism. This could explain why an excess of alcohol does not prevent loss of the alcohol blocking group, but, on the other hand, in the presence of excess alcohol, the protective alkoxy group exists in rapid equilibrium as the ether and the alcohol. Therefore, when a β-substituted propionate and primary amine are dissolved in the parent alcohol, the activated double bond will be unprotected for a small but significant amount of time, and the amine, being a stronger nucleophile than the alcohol, adds to the double bond. Because of the equilibria of these reactions, the resulting secondary amine appears to predominate over the ether. By eliminating the protic solvent, we have found that in the aminolysis reaction we can control the mechanism which appears to cause premature loss of the blocking group.

Previous attempts to prepare acrylamides having acid sensitive N-substituents such as the dialkyl acetals, did not combine the use of the blocked acrylates and aminolysis because the ester aminolysis conditions were acidic and caused decomposition of the desired product. Also it appears that prior attempts to deblock 3-aminopropionamides required unacceptable acid conditions or high temperatures for deblocking which were destructive to the sensitive substituents of the desired product. For this reason, therefore, more expensive feedstocks, such as acryloyl chloride have been used. Our invention provides a substantial commercial advantage in providing a way to make acrylamides containing the dialkyl acetal groups without expensive feedstocks and in good yields.

Other aspects and embodiments of our invention will be apparent to those skilled in the art from the foregoing disclosure without departing from the spirit or scope of our invention.

We claim:

1. A process for making an acrylamide dialkyl acetal which comprises:
    (a) reacting an acrylic acid ester with a nucleophile to form a β-substituted propionate,
    (b) separating any excess nucleophile from said β-substituted propionate,
    (c) reacting said β-substituted propionate with an amino dialkyl acetal in the presence of an aminolysis catalyst and the absence of protic solvent to form a β-substituted propionamide dialkyl acetal, and
    (d) pyrolyzing said β-substituted propionamide dialkyl acetal to form said acrylamide dialkyl acetal.

2. The process of claim 1 wherein said nucleophile is an alcohol.

3. The process of claim 1 wherein said aminolysis catalyst is an oxide, alkoxide, or alkyl oxide of titanium, zirconium, aluminum, tin, lead, antimony, bismuth, lithium, sodium or zinc.

4. The process of claim 1 wherein said pyrolyzing is carried out over a weakly basic catalyst.

5. The process of claim 1 wherein said reacting step (c) is carried out at a temperature in the range of 70° C. to 130° C.

6. A process for making N-substituted acrylamides containing an acid sensitive dialkyl acetal group which comprises:

(a) blocking the double bond of an acrylic acid ester having the formula

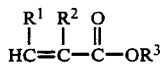

wherein $R^1$ is hydrogen, alkyl, cycloalkyl or aryl having up to 6 carbons or —$COOR^4$; $R^2$ is hydrogen, alkyl, cycloalkyl or aryl having up to 6 carbons, but at least one of $R^1$ and $R^2$ is hydrogen; and $R^3$ and $R^4$ are each alkyl of 1 to 4 carbons or phenyl; by catalytic reaction with a nucleophile;

(b) separating the blocked ester from any unreacted nucleophile;

(c) aminating said blocked ester in the presence of an aminolysis catalyst and in the absence of any protic solvent with an amino dialkyl acetal having the formula

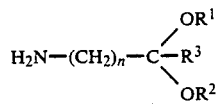

wherein $R^1$ and $R^2$ are each alkyl of 1 to 4 carbons and $R^3$ is hydrogen or alkyl of 1 to 4 carbons, and n is an integer of 1 to 10; and (d) pyrolyzing the aminated product of step (d) under non-acidic conditions to restore said double bond and form said N-substituted acrylamide.

7. The process of claim 6 wherein said ester is methyl acrylate, said amino dialkyl acetal is aminobutyraldehyde dimethyl acetal, and said N-substituted acrylamide is acrylamidobutyraldehyde dimethyl acetal.

8. The process of claim 7 wherein said nucleophile is methanol.

9. The process of claim 6 wherein said aminolysis catalyst is an oxide, alkoxide or alkyl oxide of titanium, zirconium, aluminum, tin, lead, antimony, bismuth, lithium, sodium or zinc.

10. The process of claim 8 wherein said aminolysis catalyst is titanium isopropoxide.

11. The process of claim 10 wherein the catalyst used in said blocking step (a) is sodium methoxide.

* * * * *